(12) United States Patent
Nakanishi et al.

(10) Patent No.: US 9,255,115 B2
(45) Date of Patent: Feb. 9, 2016

(54) METHOD FOR PRODUCING GLUFOSINATE P FREE ACID

(71) Applicant: MEIJI SEIKA PHARMA CO., LTD., Tokyo (JP)

(72) Inventors: Nozomu Nakanishi, Kanagawa (JP); Takashi Ando, Kanagawa (JP); Nobuto Minowa, Kanagawa (JP); Masaaki Mitomi, Kanagawa (JP)

(73) Assignee: MEIJI SEIKA PHARMA CO. LTD., Tokyo (JP)

( * ) Notice: Subject to any disclaimer, the term of this patent is extended or adjusted under 35 U.S.C. 154(b) by 0 days.

(21) Appl. No.: 14/348,376

(22) PCT Filed: Sep. 28, 2012

(86) PCT No.: PCT/JP2012/075060
§ 371 (c)(1),
(2) Date: Mar. 28, 2014

(87) PCT Pub. No.: WO2013/047738
PCT Pub. Date: Apr. 4, 2013

(65) Prior Publication Data
US 2014/0309453 A1 Oct. 16, 2014

(30) Foreign Application Priority Data

Sep. 30, 2011 (JP) ................................. 2011-217141

(51) Int. Cl.
*C07F 9/22* (2006.01)
*C07F 9/30* (2006.01)

(52) U.S. Cl.
CPC ............. *C07F 9/301* (2013.01); *C07B 2200/13* (2013.01)

(58) Field of Classification Search
CPC .............................. C07B 2200/13; C07F 9/301
See application file for complete search history.

(56) References Cited

U.S. PATENT DOCUMENTS

| 4,264,532 A | * | 4/1981 | Tsuruoka | A01N 57/20 558/115 |
| 4,499,027 A | * | 2/1985 | Minowa | A01N 57/20 504/206 |
| 4,777,279 A | * | 10/1988 | Zeiss | C07F 9/301 558/145 |
| 5,329,014 A | | 7/1994 | Shinohara et al. | |
| 6,359,162 B1 | | 3/2002 | Wilms | |
| 7,964,626 B2 | | 6/2011 | Aoki et al. | |
| 8,222,452 B2 | | 7/2012 | Maeda | |
| 2008/0146837 A1 | | 6/2008 | Minowa et al. | |
| 2009/0088575 A1 | | 4/2009 | Aoki et al. | |
| 2010/0160636 A1 | | 6/2010 | Maeda | |

FOREIGN PATENT DOCUMENTS

| CN | 1858054 A | 11/2006 |
| EP | 0 018 415 A1 | 12/1979 |
| EP | 0 009 022 A1 | 3/1980 |
| EP | 0 224 880 A1 | 6/1987 |
| EP | 0 249 188 A3 | 6/1987 |
| EP | 1 731 510 A1 | 12/2006 |
| EP | 1 864 989 A1 | 12/2007 |
| EP | 2 172 443 A1 | 4/2010 |
| JP | 54-84529 A | 7/1979 |
| JP | 54-154715 A | 12/1979 |
| JP | 57-47485 | 3/1982 |
| JP | 62-132891 A | 6/1987 |
| JP | 04-89479 A | 3/1992 |
| JP | 2001-515024 A | 9/2001 |
| WO | 2005-095355 A1 | 10/2005 |
| WO | 2006/104120 A1 | 10/2006 |
| WO | 2009-005024 A1 | 1/2009 |
| WO | WO2011129820 | * 10/2011 |

OTHER PUBLICATIONS

Extended European Search Report for Application No. 12835024.6, which was mailed on Apr. 2, 2015.
Zeiss, H.J, Enantioselective Synthesis of Both Enantiomers of Phosphinothricin via Asymmetric Hydrogenation of Alpha-Acyclamido Acrylates, Journal of Organic Chemistry, vol. 56, No. 5, Jan. 1, 1991, pp. 1783-1788.
International Preliminary Report on Patentability for PCT/JP2012/075060, which was mailed on Apr. 10, 2014.
International Search Report for PCT/JP2012/075060, which was mailed on Dec. 4, 2012.

* cited by examiner

*Primary Examiner* — Yevegeny Valenrod
*Assistant Examiner* — Blaine G Doletski
(74) *Attorney, Agent, or Firm* — Greenblum & Bernstein, P.L.C.

(57) ABSTRACT

The present invention provides a method for producing crystalline glufosinate P free acid with high purity from glufosinate P hydrochloride salt. In addition, the present invention also provides a method comprises a process of: dissolving glufosinate P hydrochloride salt in a solvent which is a mixed solvent of water and an alcohol(s) selected from the group of methanol, ethanol, propyl alcohol and isopropyl alcohol, and a ratio of water to the alcohol(s) is from 1:3 to 1:100 by volume; crystallizing glufosinate P free acid after neutralizing by addition of a base.

2 Claims, 6 Drawing Sheets

METHOD FOR PRODUCING GLUFOSINATE P FREE ACID

REFERENCE TO RELATED APPLICATION

This application is based upon and claims the benefit of the priority of JP Patent Application No. 2011-217141 (filed on Sep. 30, 2011), the disclosure thereof being incorporated herein in its entirety by reference thereto.

The present invention relates to a new production method of glufosinate P free acid which is useful as an herbicide.

TECHNICAL FIELD

Background

Glufosinate P (L-2-amino-4-(hydroxymethylphosphinyl)-butanoic acid) is an active substance of glufosinate (DL-2-amino-4-(hydroxymethylphosphinyl)-butanoic acid), which has been widely used as an active ingredient of herbicide. General methods for producing glufosinate and glufosinate P are for example, as follows:

(1) A method described in JP Patent Publication No. 2638541 (Patent Document 1) is as follows:

4-(hydroxymethylphosphinyl)-2-oxo-butyric acid is treated with one or more trans aminate enzyme(s) in the presence of glutamic acid or a salt thereof and aspartic acid or a salt thereof as an amino group donor to synthesize glufosinate P, followed by purifying it with an ion-exchange column. However, the method had a problem in that a post-treatment process is complicated and there was an industrial problem in that since the obtained powder is a non-crystalline form, its hygroscopicity is very high.

(2) A method for producing glufosinate free acid described in JP Patent Laid-Open No. 84529/1979 (Patent Document 2) is as follows: Dialkylmethylphosphonite is reacted with acrolein to form 3,3-dialkoxypropyl-methyl-phosphinic acid ester and then the resultant product is subjected to acid treatment to obtain 3-oxopropyl-methyl-phosphinic acid ester. After being subjected to the Strecker reaction, the resultant product is subjected to acid hydrolysis to obtain glufosinate hydrochloride salt. The hydrochloride salt is neutralized with caustic soda and then ethanol is added thereto. As a result, glufosinate free acid is obtained.

(3) A method for producing glufosinate ammonium salt described in Japanese Translation of PCT No. 515084/2001 (Patent Document 3) is as follows:

An addition product is synthesized from a methylphosphorus compound and an unsaturated keto compound. After being subjected to the Strecker reaction, finally, amino nitrile is subjected to acid hydrolysis, then the resultant product is treated with ammonia and as a result, glufosinate ammonium salt is obtained.

(4) A method for producing glufosinate ammonium salt described in CN 1858054 (Patent Document4) is as follows:

The Michael addition reaction takes place between a methylphosphorus compound and acrolein in the presence of an appropriate weak acid. After being subjected to the Strecker reaction, glufosinate hydrochloride salt is obtained by acid hydrolysis. After treatment with ammonia, glufosinate ammonium salt is obtained.

As exemplified in (2)-(4), even if any synthesis method is used, to synthesize glufosinate P or glufosinate, its hydrochloride salt is needed. Thus, a production method which is applicable to mass-synthesis has been needed in order to obtain glufosinate P or glufosinate with high purity as a free acid, from its hydrochloride salt.

PATENT DOCUMENTS

[Patent Document 1] JP Patent Publication No. 2638541
[Patent Document 2] JP Patent Laid-Open (Kokai) No. 84529/1979
[Patent Document 3] Japanese Translation of PCT No. 515084/2001
[Patent Document 4] Chinese Patent CN 1858054A

SUMMARY

The following analysis is given by the present inventors. The present inventors found a method for producing glufosinate P free acid which is synthesized by neutralizing glufosinate P hydrochloride salt with caustic soda, as a crystal with high purity and good yield. The present invention is based on this finding.

It is an object of the present invention to provide a method for the simple and inexpensive production of glufosinate P free acid as a crystal with high purity.

According to a first aspect of the present invention, there is provided a method for producing a compound expressed by the following formula (I):

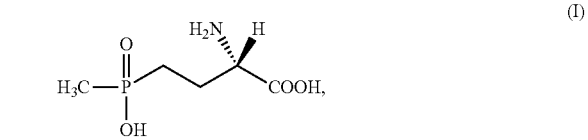

wherein the method comprises a process of:
dissolving a compound expressed by the following formula (II):

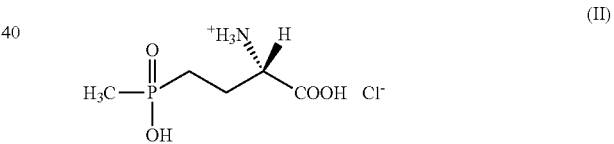

in a solvent which is a mixed solvent of water and an alcohol(s) selected from the group of methanol, ethanol, propyl alcohol and isopropyl alcohol, and a ratio of water to the alcohol(s) is from 1:3 to 1:100 by volume;
crystallizing the compound expressed by formula (I) after neutralizing by addition of a base.

According to a second aspect of the present invention, there is provided a crystalline compound expressed by formula (I) obtained by the method of the first aspect.

The production method according to the present invention is advantageous in that crystalline glufosinate P free acid which is industrially effective and having low hygroscopicity, can be produced with high purity and high yield. In addition, the production method according to the present invention is also advantageous in that glufosinate P free acid can be produced as a crystal, extremely simply and inexpensively without the need for special devices.

PREFERRED MODES

Compound Expressed by Formula (I)

Figure 1:
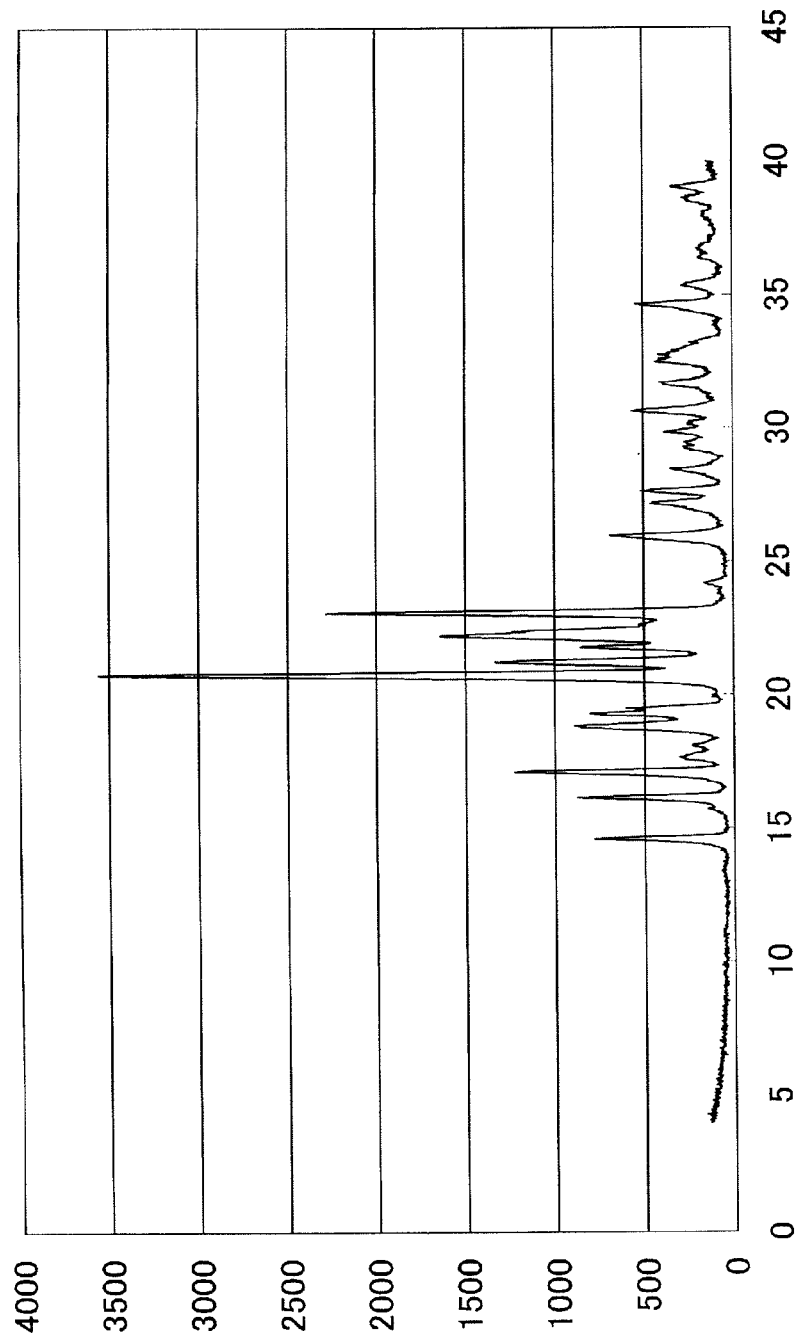
FIG. 1 is a powder X-ray diffraction diagram of crystalline glufosinate P free acid (crystal A) obtained in Example 7.

Glufosinate P free acid is expressed by the above formula (I).

Crystalline glufosinate P free acid can exist in an anhydrous form or a hydrated form, or in a mixed form thereof.

Glufosinate P free acid and its crystal can be in a salt form such as sodium salt, potassium salt, ammonium salt etc., as desired. Further, it can also be in an acid addition salt form such as hydrochloric acid, sulfuric acid, acetic acid, nitric acid etc. Glufosinate P monosodium salt (chemical name: sodium L-homoalanin-4-yl(methyl)phosphinate) is preferably exemplified as a salt of glufosinate P obtained from crystalline glufosinate P free acid of the present invention.

Production Method of Compound of Formula (I)

According to the present invention, the compound of formula (I) with high purity can be produced by that glufosinate P hydrochloride salt expressed by formula (II) is neutralized by adding a base in a water-alcohol type solvent, followed by recovering the compound expressed by formula (I) by crystallization.

The compound expressed by formula (II) can be synthesized according to such a known method as described in WO 2006/104120, the entire disclosure thereof being incorporated herein by reference thereto.

As an alcoholic solvent(s) used for dissolving the compound of formula (II), methanol, ethanol, propyl alcohol and isopropyl alcohol etc. may be exemplified, preferably, methanol. These alcoholic solvents may be used alone, or two or more kinds of them may be used in combination. A ratio of water to the alcoholic solvent(s) is selected from 1:3 to 1:100 by volume, and preferably, a mixed solvent is water and methanol or water and ethanol, more preferably, water and methanol.

There is no particular limitation of an amount of water and the alcoholic solvent(s) as long as the mixed solvent can dissolve the compound of formula (II). For example, the mixed solvent can be used in an amount of 2 to 30 w/v based on the compound of formula (II).

As a "base" used for neutralization, a hydroxide of alkali metal or alkali earth metal, carbonate, alcohol salt etc. are exemplified, for example, bases such as lithium hydroxide, sodium hydroxide, potassium hydroxide, cesium hydroxide, lithium carbonate, sodium carbonate, potassium carbonate, cesium carbonate, sodium hydrogen carbonate, potassium hydrogen carbonate, sodium ethoxide, sodium methoxide etc. are exemplified, preferably, sodium hydroxide, or sodium methoxide, more preferably, sodium hydroxide.

An amount of a base used for reaction may be used, for example, in 0.8 to 1.2 equivalents based on the compound of formula (II).

The addition of a base is preferably conducted gradually over several minutes to several hours. A time required for the addition can be defined appropriately, depending on a reaction scale.

The addition of a base may be conducted preferably within a range of −10 to 50 deg. C, for example.

As a preferred exemplary embodiment of the production method of the present invention, the production method of the compound expressed by formula (I) is exemplified, the method comprising a process of:

adding sodium hydroxide or sodium methoxide to the compound of formula (II) which is dissolved in a water-methanol mixed solvent (in which the ratio of water to methanol is from 1:3 to 1:100 by volume), to neutralize; and
recovering the crystallized compound of formula (I).

As a more preferred exemplary embodiment of the production method of the present invention, the production method of the compound expressed by formula (I) is exemplified, the method comprising a process of:

adding sodium hydroxide or sodium methoxide to the compound of formula (II) which is dissolved in a water-methanol mixed solvent (in which the ratio of water to methanol is from 1:3 to 1:85 by volume), to neutralize; and
recovering the crystallized compound of formula (I).

According to the production method of the present invention, glufosinate P free acid can be obtained in 83 to 100% purity, preferably 90 to 100%, more preferably 92 to 100% purity.

According to the production method of the present invention, glufosinate P free acid which is the compound of formula (I) can be obtained in a yield of 85 to 100%, preferably 92 to 100% from the compound of formula (II).

Figure 3:
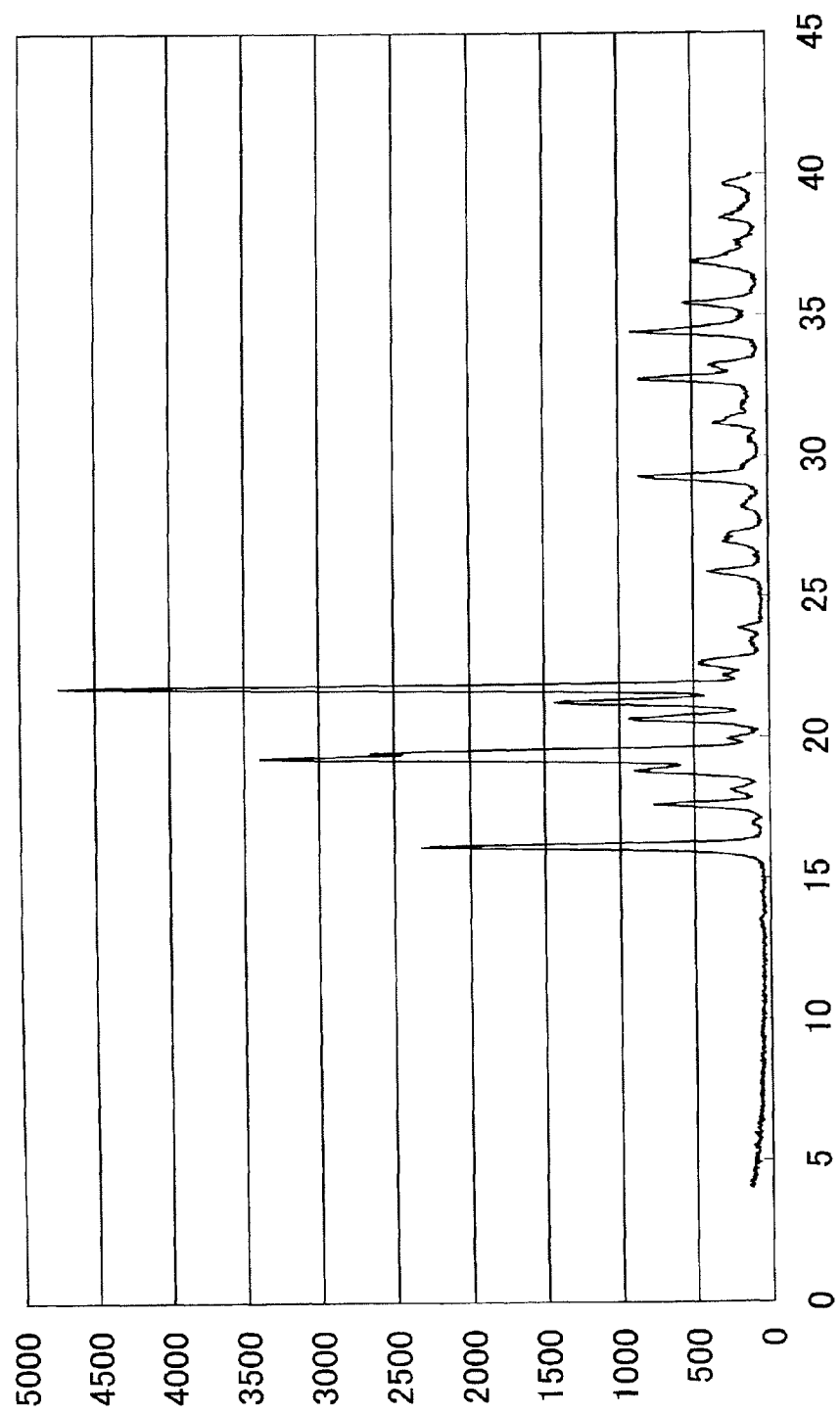
FIG. 3 is a powder X-ray diffraction diagram of crystalline glufosinate P free acid (crystal B) obtained in Example 8.

In powder X-ray diffraction analysis, it is characterized that the crystallized compound of formula (I) shows a diffraction peak pattern shown in FIG. 1 or FIG. 3 depending on whether the compound is an anhydrous form or a hydrated form. In the diffraction peak pattern shown in FIG. 1, peaks derived from the hydrated form of glufosinate P (crystal A), which have at least 15% of relative intensity assuming that the intensity of the peak of 2θ=20.78° is 100%, are as follows:

TABLE 1

| Diffraction angles (2θ) |
|---|
| 14.6 ± 0.2° |
| 17.1 ± 0.2° |
| 20.8 ± 0.2° |
| 22.2 ± 0.2° |
| 23.1 ± 0.2° |
| 26.0 ± 0.2° |

In addition, in the diffraction peak pattern shown in FIG. 3, peaks derived from the anhydrous form of glufosinate P (crystal B), which have at least 15% of relative intensity assuming that the intensity of the peak of 2θ=21.80° is 100%, are as follows:

TABLE 2

| Diffraction angles (2θ) |
| --- |
| 16.1 ± 0.2° |
| 17.6 ± 0.2° |
| 19.3 ± 0.2° |
| 19.5 ± 0.2° |
| 21.8 ± 0.2° |

The diffraction peaks obtained by the above powder X-ray diffraction analysis include an error range of about ±0.2° caused by instruments for measurement, environments for analysis etc.

The compound expressed by formula (I) can be used as an herbicide.

EXAMPLES

Hereinafter, the present invention is specifically described by way of Examples, but is not limited to these Examples.

Instruments for Analysis and Conditions for Measurement
(Purity)

Purities described in Examples show purities quantified by HPLC using glufosinate P reference standard with known purity as a reference substance under the following conditions:

Detector: Ultraviolet-visible light absorption spectrometry
Column: Capcell Pak C18-ACR (4.6 mm×250 mm)
Mobile phase: 5 mM octanesulfonic acid sodium aqueous solution (pH 2.5)
Flow rate: 1 mL/minute
Column temperature: 40 deg. C.
(Powder X-Ray Diffraction)

Data of powder X-ray diffraction described in Examples show values measured under the following conditions:

Instrument: RINT-2200 (Rigaku CORPORATION)
X-ray: Cu-Kα (40 kV, 20 mA)
Scan range: 4-40° Sampling range: 0.02° Scan speed: 1°/minute
(Differential Scanning Calorimetry Analysis (DSC))

Data of DSC described in Examples show values measured under the following conditions:

Instrument: DSC-60
Sample cell: Aluminium
Temperature range: 50-250 deg. C (Temperature rising rate: 10 deg. C./minute)

Example 1

Production of Glufosinate P Free Acid 50 mmol of glufosinate P hydrochloride salt was dissolved in 10 mL of water and 90 mL of methanol, and then 25 mL of methanol in which 1 equivalent of sodium hydroxide was dissolved, was added thereto. After adding a seed crystal obtained in Reference example 2, the resultant solution was stirred for 15 minutes at room temperature and then cooled in ice and stirred for 3 hours and a half. The precipitated crystal was collected by filtration and then subjected to vacuum dehydration. 9.35 g of the objective compound was obtained (yield: 95.9%, purity: 91.7%).

Example 2

Production of Glufosinate P Free Acid 50 mmol of glufosinate P hydrochloride salt was dissolved in 17 mL of water and then 4.17 g of water in which 1 equivalent of sodium hydroxide was dissolved, was added thereto. After adding 60 mL of methanol, a seed crystal obtained in Reference example 2 was added thereto. The resultant solution was stirred for 15 minutes at room temperature and then cooled in ice and stirred for 3 hours and a half. The precipitated crystal was collected by filtration and then subjected to vacuum dehydration. 9.09 g of the objective compound was obtained (yield: 92.4%, purity: 92.0%).

Example 3

Production of Glufosinate P Free Acid 50 mmol of glufosinate P hydrochloride salt was dissolved in 20 mL of water and 180 mL of methanol, and then 1 equivalent of sodium hydroxide was added thereto. After adding a seed crystal obtained in Reference example 2, the resultant solution was stirred for 15 minutes at room temperature and then cooled in ice and stirred for 3 hours and a half. The precipitated crystal was collected by filtration and then subjected to vacuum dehydration. 9.09 g of the objective compound was obtained (yield: 91.3%, purity: 98.8%).

Example 4

Production of Glufosinate Free Acid 50 mmol of glufosinate P hydrochloride salt was dissolved in 210 mL of methanol and then 2.17 g of water in which 1 equivalent of sodium hydroxide was added and dissolved, was added thereto. After adding a seed crystal obtained in Reference example 2, the resultant solution was stirred for 4 hours and a half at room temperature. The precipitated crystal was collected by filtration and then subjected to vacuum dehydration. 8.84 g of the objective compound was obtained (yield: 92.3%, purity: 95.6%).

Example 5

Production of Glufosinate P Free Acid 50 mmol of glufosinate P hydrochloride salt was dissolved in 10 mL of water and 125 mL of methanol and then 25 mL of methanol in which 1 equivalent of sodium hydroxide was added and dissolved, was added thereto. After adding a seed crystal obtained in Reference example 2, the resultant solution was stirred for 30 minutes at room temperature and then cooled in ice and stirred for 3 hours and a half. The precipitated crystal was collected by filtration and then subjected to vacuum dehydration. 9.02 g of the objective compound was obtained (yield: 96.0%, purity: 96.3%).

Example 6

Production of Glufosinate P Free Acid 1 mol of glufosinate P hydrochloride salt was dissolved in 200 mL of water and 2500 mL of methanol and then 500 mL of methanol in which 1 equivalent of sodium hydroxide was added and dissolved, was added thereto. After adding a seed crystal obtained in Reference example 2, the resultant solution was stirred for 30 minutes at room temperature and then cooled in ice and stirred for 3 hours and a half. The precipitated crystal was collected by filtration and then subjected to vacuum dehydration. 173.4 g of the objective compound of crystal B was obtained (yield: 94.2%, purity: 97.3%).

Example 7

Figure 2:
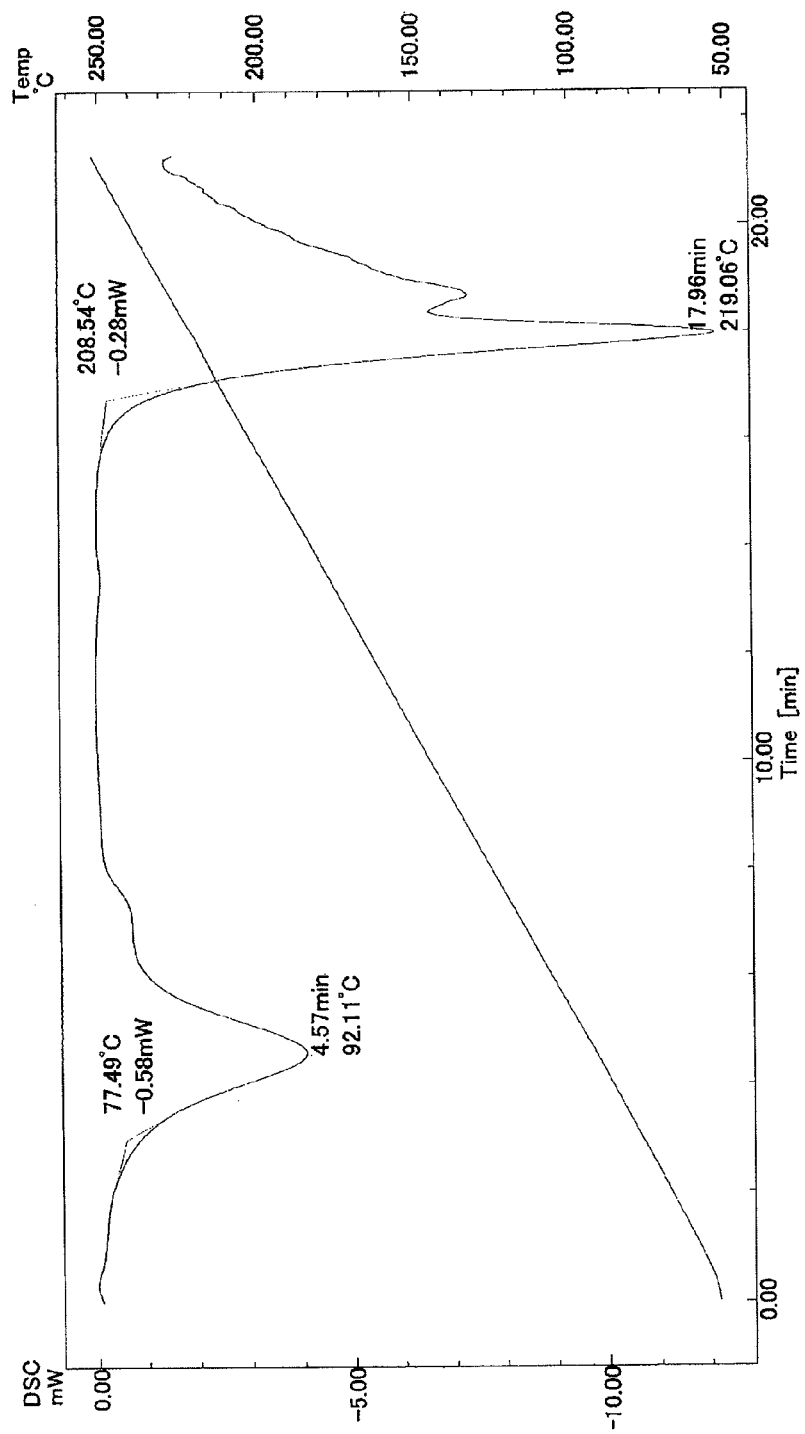
FIG. 2 is an analysis chart of Differential Scanning calorimetry measurement (DSC) of crystalline glufosinate P free acid (crystal A) obtained in Example 7.

Production of Glufosinate P Free Acid 30 g of glufosinate P hydrochloride salt was dissolved in 27.6 mL of water and 314 mL of methanol and then 100 mL of methanol in which 1.01 equivalent of sodium hydroxide was added and dissolved, was added thereto. After adding a seed crystal obtained in Reference example 2, the resultant solution was stirred for 21 hours at 0 to 2 deg. C. The precipitated crystal was collected by filtration and then subjected to vacuum dehydration. 23.4 g of the objective compound of crystal A was obtained (yield: 93.3%, purity: 91.7%). The powder X-ray diffraction diagram and DSC chart of the obtained crystal A were shown in FIG. 1 and FIG. 2 respectively.

In the powder X-ray diffraction of crystal A, peaks which have at least 15% of relative intensity assuming that the intensity of the peak of $2\theta=20.78°$ is 100%, were shown at $2\theta=14.62°, 16.20°, 17.14°, 18.78°, 19.30°, 20.78°, 21.22°, 21.78°, 22.22°, 23.08°, 25.98°, 27.64°$.

Example 8

Figure 4:
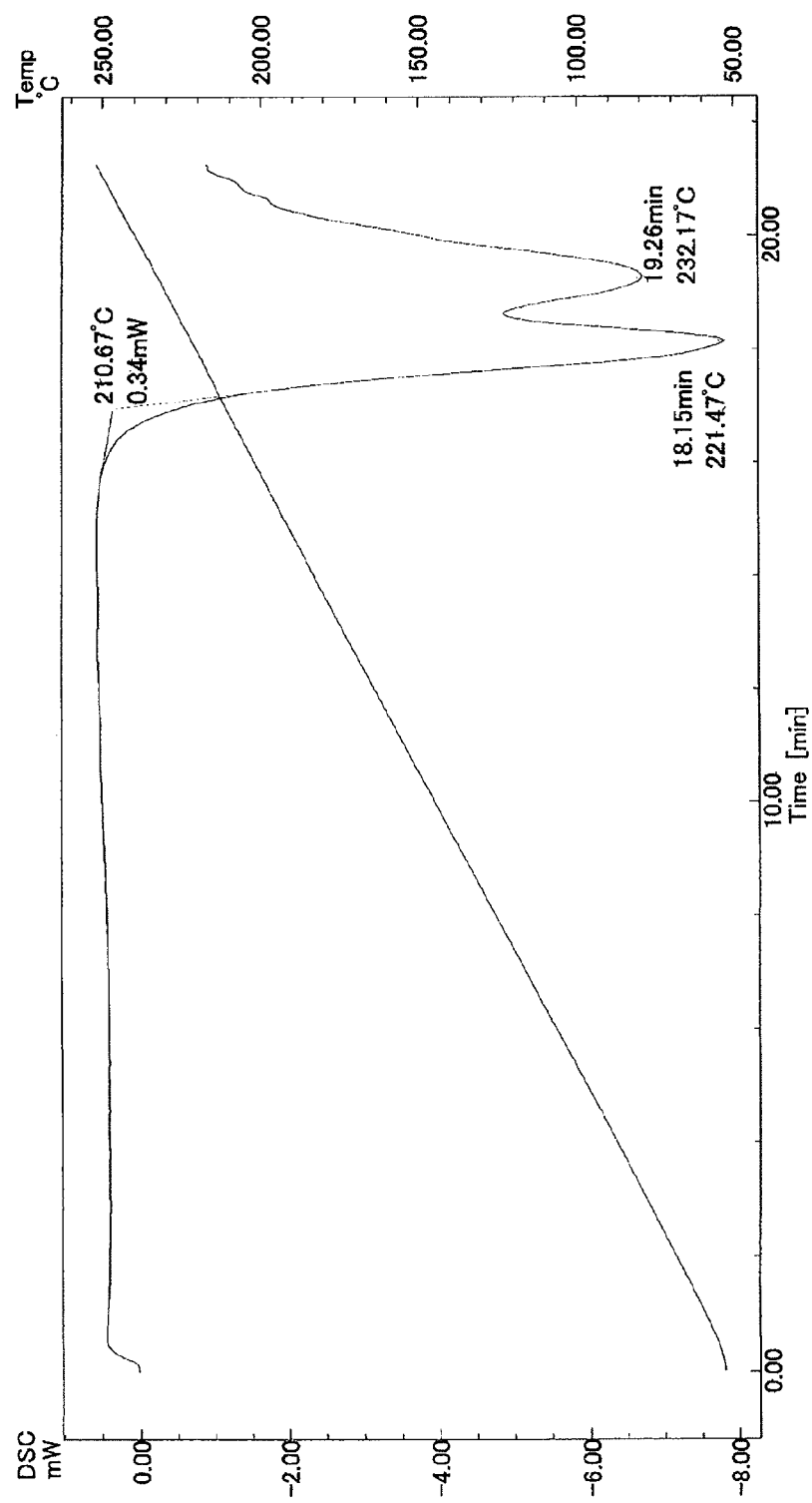
FIG. 4 is an analysis chart of Differential Scanning calorimetry measurement (DSC) of crystalline glufosinate P free acid (crystal B) obtained in Example 8.
Figure 5:
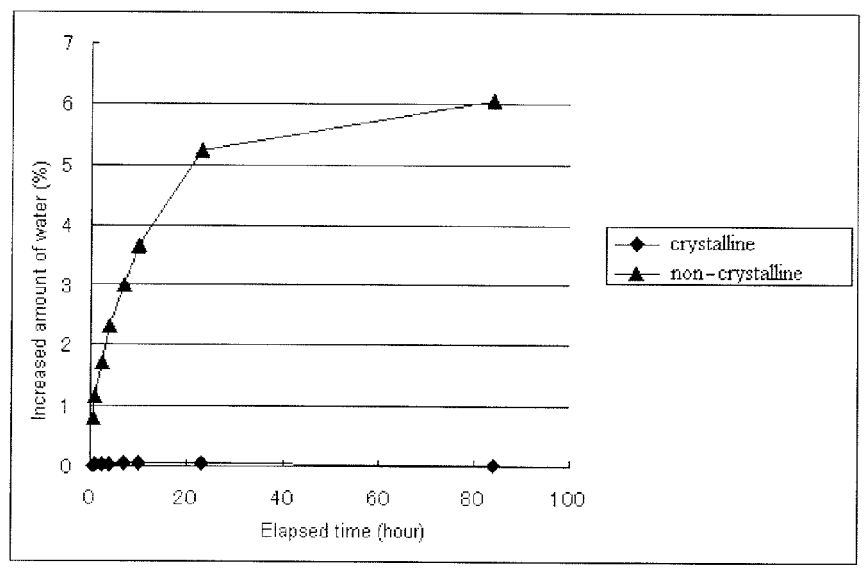
FIG. 5 is a graph showing results of the hygroscopic equilibrium test of non-crystalline glufosinate P free acid and crystalline glufosinate P free acid obtained in Example 6 at 30% relative humidity.
Figure 6:
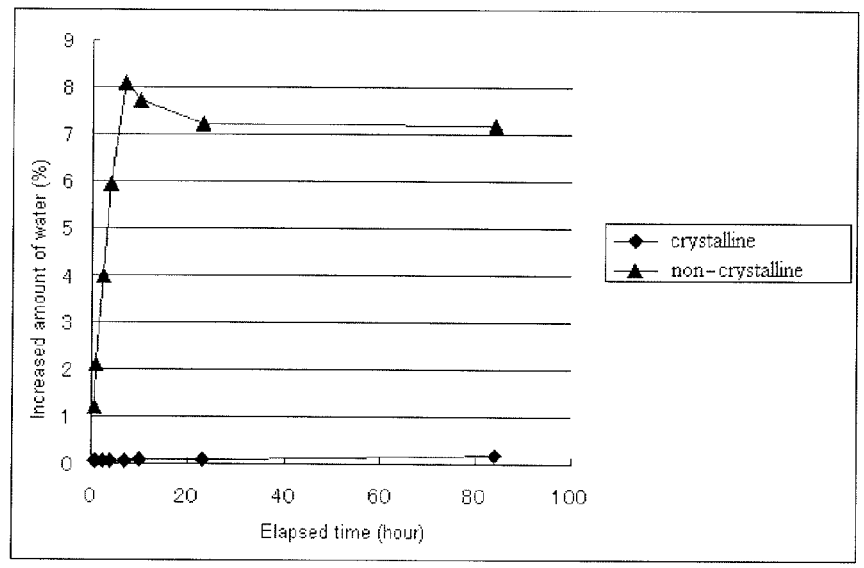
FIG. 6 is a graph showing results of the hygroscopic equilibrium test of non-crystalline glufosinate P free acid and crystalline glufosinate P free acid obtained in Example 6 at 52% relative humidity.
Figure 7:
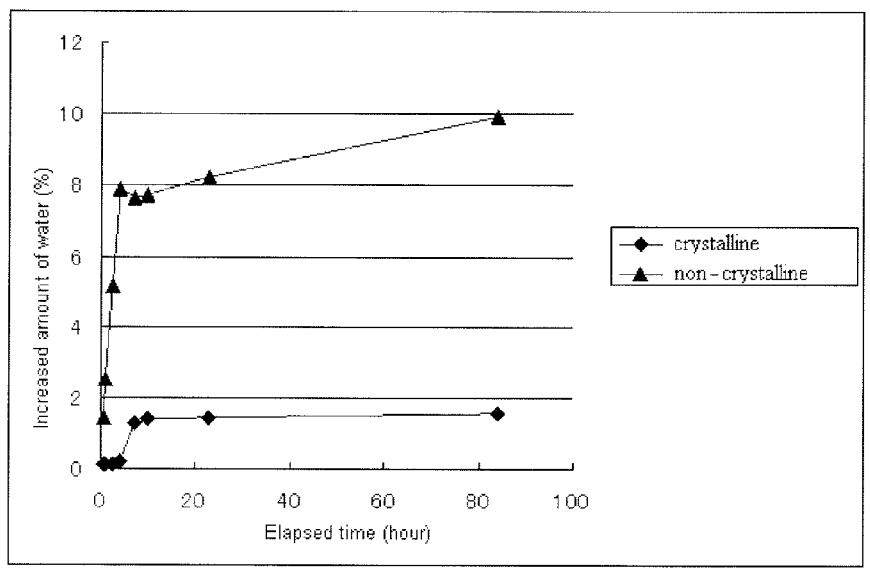
FIG. 7 is a graph showing results of the hygroscopic equilibrium test of non-crystalline glufosinate P free acid and crystalline glufosinate P free acid obtained in Example 6 at 75% relative humidity.
Figure 8:
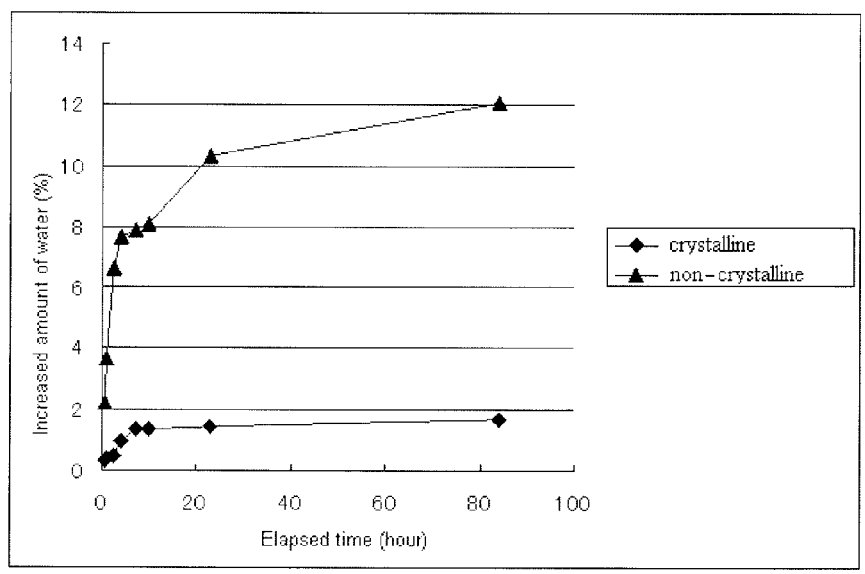
FIG. 8 is a graph showing results of the hygroscopic equilibrium test of non-crystalline glufosinate P free acid and crystalline glufosinate P free acid obtained in Example 6 at 91% relative humidity.

Production of Glufosinate P Free Acid 10 g of glufosinate P hydrochloride salt was dissolved in 138 mL of methanol and then 9.2 mL of water in which 1 equivalent of sodium hydroxide was added and dissolved, was added thereto. After adding a seed crystal obtained in Reference example 2, the resultant solution was stirred for 2 hours at 40 to 50 deg. C and then stirred for 20 hours at room temperature. The precipitated crystal was collected by filtration and then subjected to vacuum dehydration. 7.4 g of the objective compound of crystal B was obtained (yield: 91.8%, purity: 97.4%). The powder X-ray diffraction diagram and DSC chart of the obtained crystal B were shown in FIG. 3 and FIG. 4 respectively.

In the powder X-ray diffraction of crystal B, peaks which have at least 15% of relative intensity assuming that the intensity of the peak of $2\theta=21.80°$ is 100%, were shown at $2\theta=16.14°, 17.60°, 18.82°, 19.28°, 19.52°, 20.64°, 21.24°, 21.80°$.

Example 9

Production of Glufosinate P Free Acid 10 g of glufosinate P hydrochloride salt was dissolved in 1.8 mL of water and 138 mL of methanol and then 10 mL of methanol in which 1 equivalent of sodium methoxide was added and dissolved, was added thereto. After adding a seed crystal obtained in Reference example 2, the resultant solution was stirred for 2 hours at 40 to 50 deg. C and then stirred for 20 hours at room temperature. The precipitated crystal was collected by filtration and then subjected to vacuum dehydration. 7.7 g of the objective compound was obtained (yield: 94.9%, purity: 95.4%).

Examples 10 to 21

Production of Glufosinate P Free Acid

Glufosinate P free acid was produced by using the method according to Example 1 under conditions shown in Table 3. Yield and purity of glufosinate P free acid obtained in each Example were shown in Table 3.

As demonstrated in Examples 7 and 8, the crystalline property is determined by the presence of specific peaks in the X-ray diffraction spectra, and particularly manifest by the peak intensity of at least 15% of the relative intensity assuming that the intensity of the peak of $2\theta=20.78°$ (Example 7) or $2\theta=21.80°$ (Example 8) is 100%. Note this feature is observed or will be observed even in the Examples for which the X-ray diffraction data is not shown.

TABLE 3

Yield and purity of glufosinate P free acid under various conditions

| Example No. | Glufosinate P hydrochloride salt | Water (mL) | Methanol (mL) | Purity (%) | Yield (%) |
|---|---|---|---|---|---|
| 1 | 50 mmol(10.87 g) | 10 | 115 | 91.7 | 95.9 |
| 2 | 50 mmol(10.87 g) | 20 | 60 | 92 | 92.4 |
| 3 | 50 mmol(10.87 g) | 20 | 180 | 98.8 | 91.3 |
| 4 | 50 mmol(10.87 g) | 2.17 | 210 | 95.6 | 92.3 |
| 5 | 50 mmol(10.87 g) | 10 | 150 | 96.3 | 96.0 |
| 6 | 1 mol(217.5 g) | 200 | 3000 | 97.3 | 94.2 |
| 7 | 138 mmol(30 g) | 27.6 | 414 | 91.7 | 93.3 |
| 8 | 45.6 mmol(10 g) | 9.2 | 138 | 97.4 | 91.8 |
| 9 | 45.6 mmol(10 g) | 1.8 | 148 | 95.4 | 94.9 |
| 10 | 50 mmol(10.87 g) | 10 | 190 | 97.3 | 94.4 |
| 11 | 50 mmol(10.87 g) | 10 | 165 | 98.1 | 95.7 |
| 12 | 50 mmol(10.87 g) | 10 | 90 | 92.5 | 97.0 |
| 13 | 50 mmol(10.87 g) | 20 | 80 | 90.9 | 92.1 |
| 14 | 50 mmol(10.87 g) | 20 | 40 | 90.5 | 88.4 |
| 15 | 50 mmol(10.87 g) | 13.9 | 41.8 | 87 | 91.1 |
| 16 | 50 mmol(10.87 g) | 10 | 140 | 98.2 | 95.3 |
| 17 | 50 mmol(10.87 g) | 15 | 60 | 83.4 | 90.6 |
| 18 | 50 mmol(10.87 g) | 15 | 85 | 87.6 | 93.9 |
| 19 | 50 mmol(10.87 g) | 15 | 110 | 97.3 | 92.4 |
| 20 | 45.6 mmol(10 g) | 3.6 | 138 | 94.2 | 95.6 |
| 21 | 45.6 mmol(10 g) | 10 | 40 | 90.1 | 85.9 |

Example 22

Hygroscopic Equilibrium of Non-Crystalline and Crystalline Glufosinate P Free Acid Results of hygroscopic equilibrium test for non-crystalline glufosinate P free acid produced according to the methods described in Examples 1 and 2 in JP Patent Laid-Open (Kokai) No. 47485/1982 and crystalline glufosinate P free acid obtained in Example 6 (crystal B) were shown in FIGS. 5 to 8. The hygroscopic equilibrium test was conducted by measuring the weight of glufosinate P free acid overtime after placing a saturated aqueous solution in which each salt described below was dissolved, into a desiccator. The hygroscopicity of crystalline glufosinate P free acid was much lower than that of non-crystalline glufosinate P free acid.

30% relative humidity: Calcium chloride dihydrate
52% relative humidity: Calcium nitrate tetrahydrate
75% relative humidity: Sodium chloride
91% relative humidity: Sodium tartrate dihydrate

Reference Example 1

3.3 g of glufosinate P hydrochloride salt was dissolved in 3 mL of water and then the pH of the solution was adjusted to 3.12 by 5N-sodium hydroxide aqueous solution. After adding 8 mL of ethanol, the resultant solution was cooled in ice and stirred for 5 hours. The precipitated crystal was collected by filtration and then subjected to vacuum dehydration. 1.18 g of the objective compound was obtained (yield: 42.8%, purity: 86.7%).

Reference Example 2

Production of Seed Crystal of Glyfosinate P 140 g of glufosinate P was purified with an ion-exchange resin according to the method described in JP Patent Publication No. 2638541, and then the collected fractions containing glufosinate P were concentrated. The methanol was added to the concentrate to crystallize. As a result, 82.4 g of the seed crystal of glufosinate P was obtained (yield: 58.9%, purity: 99.68%).

Each disclosure of prior art reference of the above Patent Documents etc. is incorporated herein in its entirety by reference thereto. The particular exemplary embodiments or examples may be modified or adjusted within the scope of the entire disclosure of the present invention, inclusive of claims, based on the fundamental technical concept of the invention. In addition, a variety of combinations or selections of elements disclosed herein (including each element of each claim, each element of each example and each element of each drawing etc.) may be made within the context of the claims. That is, the present invention may cover a wide variety of modifications or corrections that may occur to those skilled in the art in accordance with the entire disclosure of the present invention, inclusive of claims, and the technical concept of the present invention. Particularly, any numerical range disclosed herein should be interpreted that any intermediate values or subranges falling within the disclosed range are also concretely disclosed even without specific recital thereof.

What is claimed is:

1. A method for producing a compound expressed by the following formula (I):

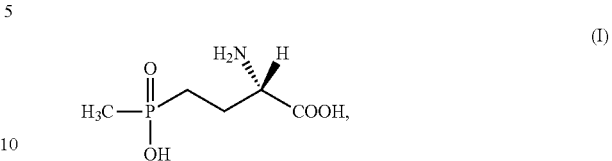

the method comprising:
dissolving a compound expressed by the following formula (II):

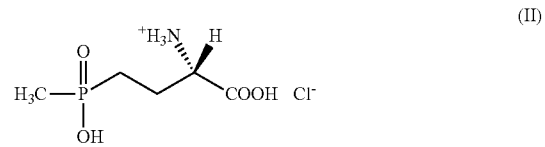

in a solvent which is a mixed solvent of water and methanol, and a ratio of water to methanol is from 1:3 to 1:100 by volume;
neutralizing the resultant solution by adding a base; and thereafter crystallizing the compound expressed by formula (I).

2. The method defined in claim 1, wherein the base is sodium hydroxide or sodium methoxide.

* * * * *